(12) United States Patent
Sutter et al.

(10) Patent No.: US 7,513,897 B2
(45) Date of Patent: Apr. 7, 2009

(54) COAGULATION TWEEZERS WITH LIMITER OPENING

(75) Inventors: Bert Sutter, Emmendingen (DE); Dirk Weitkamp, Waldkirch (DE); Hermann Sutter, Gundelfingen (DE)

(73) Assignee: Sutter Medizintechnik GmbH, Freiburg (DE)

( * ) Notice: Subject to any disclaimer, the term of this patent is extended or adjusted under 35 U.S.C. 154(b) by 0 days.

(21) Appl. No.: 11/874,471

(22) Filed: Oct. 18, 2007

(65) Prior Publication Data

US 2008/0103499 A1 May 1, 2008

(30) Foreign Application Priority Data

Oct. 28, 2006 (DE) .................... 10 2006 050 960.9

(51) Int. Cl.
*A61B 18/14* (2006.01)
(52) U.S. Cl. .................... 606/51; 606/210
(58) Field of Classification Search ............ 606/51, 606/52, 210
See application file for complete search history.

(56) References Cited

U.S. PATENT DOCUMENTS 4,461,297 A * 7/1984 Sutter .................... 606/210
5,876,420 A * 3/1999 Noll et al. ................ 606/208

FOREIGN PATENT DOCUMENTS

| DE | 3110666 | | 11/1982 | | |
| DE | 3427946 | * | 11/1985 | .............. | 606/51 |
| DE | 3427947 | * | 1/1986 | .............. | 606/51 |

* cited by examiner

*Primary Examiner*—Lee S Cohen
(74) *Attorney, Agent, or Firm*—Volpe and Koenig, P.C.

(57) ABSTRACT

Coagulation tweezers (1) provided with two tweezers legs (2) and (3), with their mutual pivoting apart from each other being limited by a stop element (6) and a counter stop element (7). Here, the protrusion or head (10) of the stop element (6), during the opening or closing the legs (2) and (3) of the tweezers, is movable inside the counter stop element (7) in reference thereto, and is spaced apart a distance in the radial direction during its relative displacement or pivotal path movement in reference to the interior longitudinal cavity (12) of the counter stop element (7) so that during normal pivotal motions of the tweezers no friction develops by these stop elements.

15 Claims, 2 Drawing Sheets

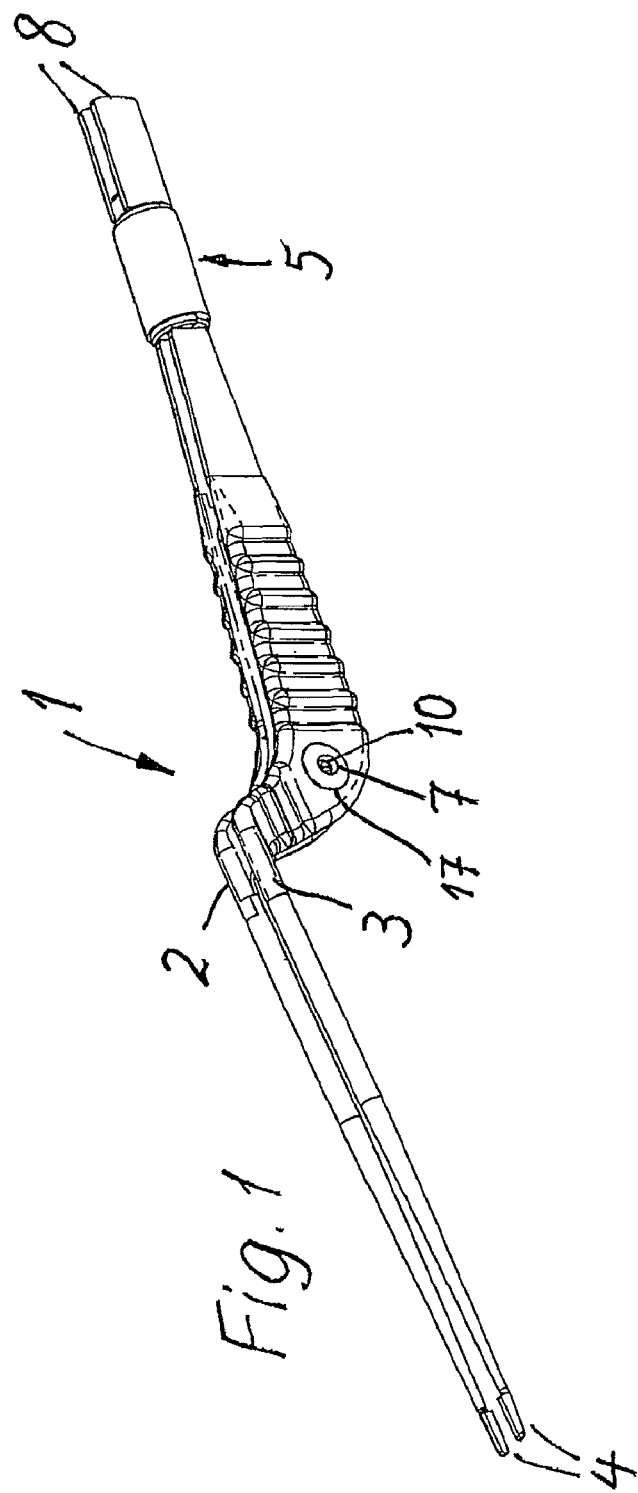
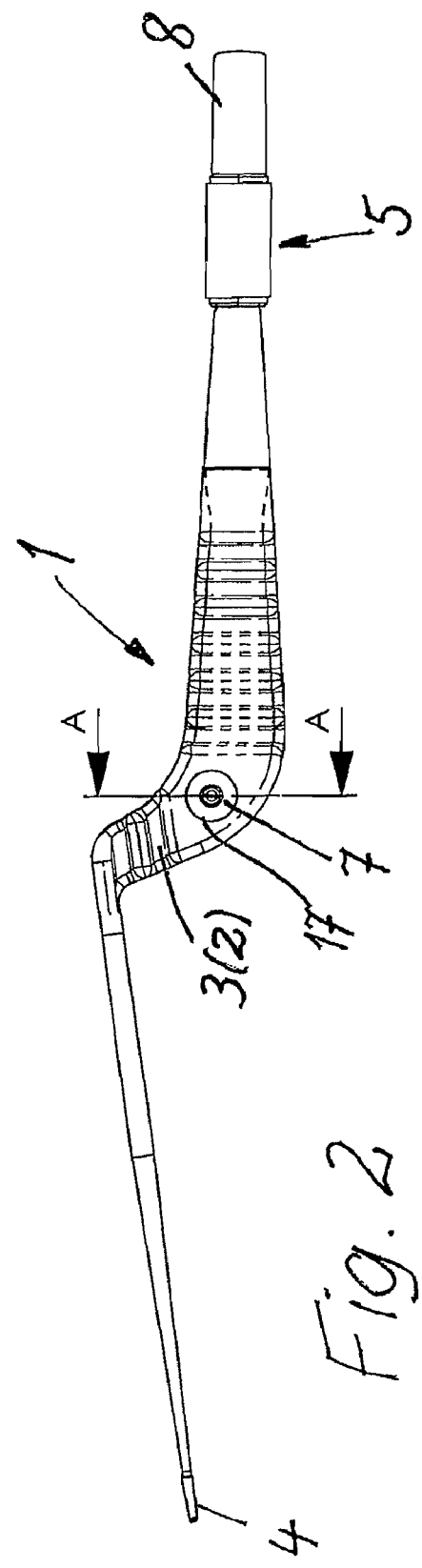

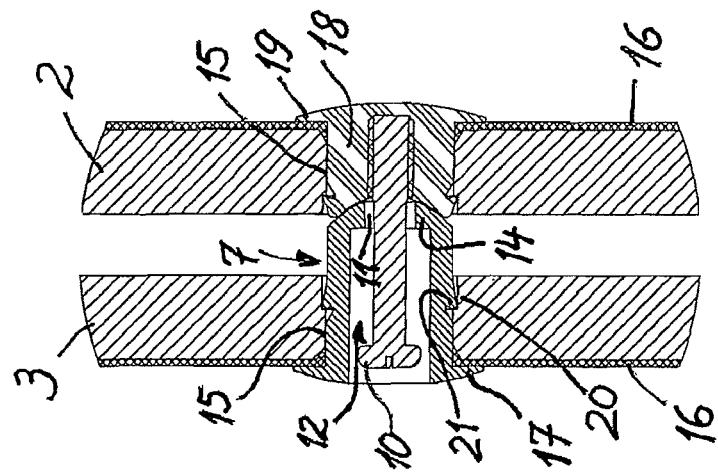
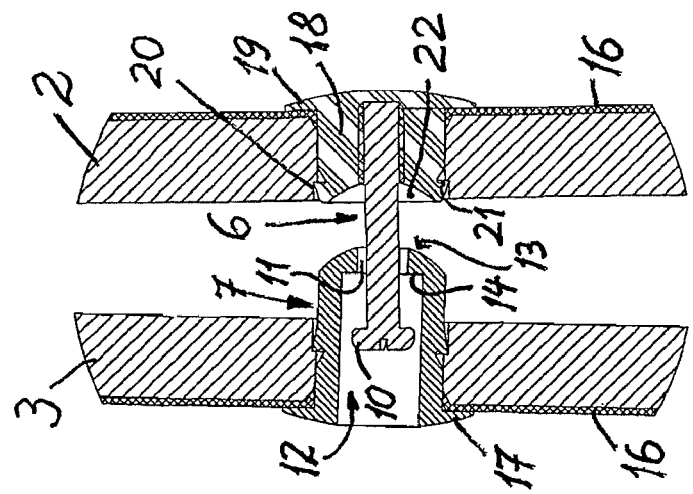
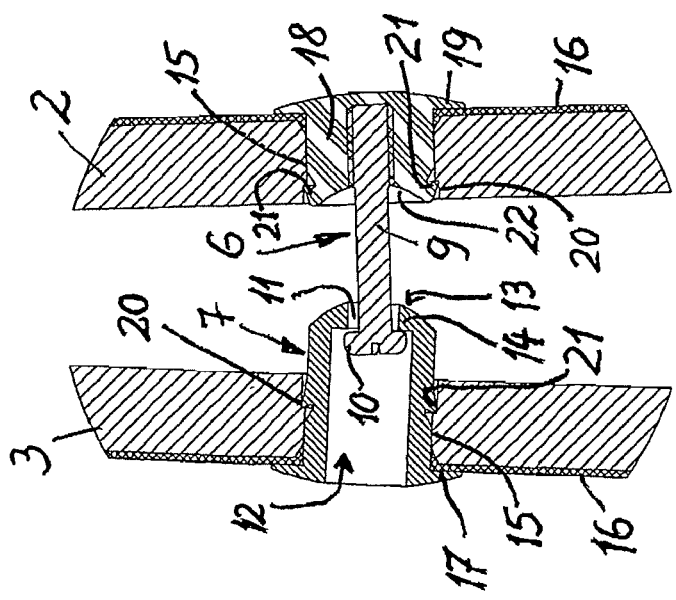

COAGULATION TWEEZERS WITH LIMITER OPENING

BACKGROUND

The invention relates to coagulation tweezers, with the legs of the tweezers merging from their operational tips to a common connecting end and with the operational tips and the connecting end being spaced apart from each other even in the closed position of the operational tips, with a stop element and a counter stop element being provided inside the perimeter of the coagulation tweezers to limit the opening of the legs of the tweezers, with the stop element being formed as a pin or shaft with a protrusion or head located at its free end, arranged laterally or radially, which is fastened at or in the first leg of the tweezers with its end facing away from this protrusion or head and with the counter stop element mounted at the second leg of the tweezers, being provided as a part engaging through the stop element, with its penetration opening having a smaller cross-section than the protrusion or head of the stop element.

Tweezers of this type are known from DE 3 110 666 C2. Here, the counter stop element is embodied as a guidance sheath, with the head of the pin serving as a stop element gliding along the interior wall in a guiding fashion during the opening and closing motion of the legs of the tweezers, namely during the entire motion of the two legs of the tweezers in reference to each other. Here, the protrusion or head of this pin prevents the legs of the tweezers from developing too wide of an opening angle, thus limiting the opening path.

In practice it has been difficult to realize via known production technology the mutual relative motions of the stop element and the counter stop element during the operation of the tweezers because these relative motions occur over a curved path; however, a pin and a sheath must be embodied straight for a cost-effective production. In practice it has shown that here at least the pin embodied as the stop element must be bent approximately equivalent to the pivotal motion, which results in a substantially more expensive production and assembly of the coagulation tweezers, particularly because in the inserted position, the curvature of the pin must also be aligned according to the progression of the pivotal motion.

SUMMARY

Therefore, the object is to provide coagulation tweezers of the type defined at the outset, in which the pin carrying the stop for the opening motion requires no preliminary curvature and yet the advantage remains that the opening path of the tweezers is limited.

In order to meet this objective, the coagulation tweezers defined at the outset are arranged so that the protrusion or head that is movable inside the counter stop element in reference thereto during the opening and closing of the legs of the tweezers is spaced apart in the radial direction from the counter stop element during its relative displacement over the pivotal path.

Surprisingly, the protrusion or head of the pin spaced apart in reference to the counter stop element provides no guidance during the mutual pivotal motion; however, it still limits the opening path of the legs of the tweezers. However, the stop element embodied as a pin with a protrusion or a head can prevent wider lateral motions of the legs of the tweezers perpendicular to the opening and closing path, because in case of an excessive lateral motion the pin contacts the counter stop element in the lateral direction and forms a stop. This way, the stop element, which remains without any contact in reference to the counter stop element during a correct motion of the legs of the tweezers, contributes to the centering means preferably provided at the legs of the tweezers for them to approach each other for the final position, and the centering occurs in a manner known per se such that the operational tips of the tweezers are precisely guided together.

Here, the protrusion or head may have a radial distance in reference to the interior side of the counter stop element over the entire pivotal path. This achieves the result that even at the very beginning, the closing motion of the legs of the tweezers occurs without any friction between the protrusion or head and the counter stop element, i.e. when the legs of the tweezers are guided together no initial resistance is to be overcome based on friction, which could compromise the precision of the motion.

It is therefore beneficial when the protrusion or head of the stop element is at spaced apart in the radial direction from the interior of the counter stop element at the positions equivalent to the opening of the tweezers or in both end positions. Although the opening path of the legs of the tweezers is limited and any excessive mutual lateral motion is also prevented, the legs of the tweezers may be moved by the operator easily and thus very precisely.

It is particularly beneficial when the counter stop element is a hollow body or cage or sheath extending axially approximately in the direction of the pivotal motion, which has at its face located in the intermediate space between the legs of the tweezers a cap or base with a penetrating opening for the pin or the shaft of the stop element, with the sheath part being approximately equivalent to the guiding sheath of DE 3 110 666 C2. Such a sheath part and/or a sheath serving as a counter stop has the advantage that it may comprise an electrically insulating material and thus contributes to the electric safety of the coagulation tweezers. Furthermore, it can be produced and mounted in a simple fashion.

The cross-section and/or the size of the penetration opening of the hollow body or the sheath part of the counter stop element can be larger than the cross-section of the pin and the brim of the penetrating opening may be provided with such a radial distance from the pin that the pin can be moved through the penetrating opening during the pivoting of the legs of the tweezers over the entire or at least a portion of the pivotal path with play or without any contact. In this manner, the protrusion or head serving as a stop is not only held without any contact in reference to the counter stop element during the pivotal motion of the legs of the tweezers, but this also applies to the pin in the area of the penetrating opening.

It is particularly beneficial for the assembly when the counter stop element is embodied such that it can be inserted in a form-fitting manner from the outside of the first leg of the tweezers facing away of the second leg of the tweezers into an opening provided there or form-fittingly mounted thereto, for example it can be snapped in, engaged, or screwed in. The counter stop element beneficially embodied as a sheath or sheath element therefore only needs to be pushed or snapped or perhaps screwed in from the outside of the second leg of the tweezers into the opening provided there in order to be fastened. This avoids having to bring this counter stop element between the legs of the tweezers during assembly and forcing an assembly from the intermediate space of the legs of the tweezers.

Another beneficial embodiment of the invention, facilitated by the assembly from the outside of the legs of the tweezers, may be that the counter stop element embodied as a sheath or sheath part is provided with a brim or protrusion at the outside of the second leg of the tweezers carrying it or an insulating coating provided there, particularly an edge encircling it in a flange-like manner. In this way the insulation can be improved, particularly when the sheath part comprises an electrically insulating material.

In order to anchor the pin of the stop element to the first leg of the tweezers a fastening element, that can be inserted from its outside, can be provided with an edge, flange, or protrusion to encompass the first leg of the tweezers or the insulating coating provided thereto at the outside, in which the pin is mounted in a protruding fashion to the intermediate space of the legs of the tweezers, in one piece or particularly in an undetachable manner. This allows for a simple assembly from the outside of the legs of the tweezers, which is simpler than an assembly from the inside or even by way of a piercing assembly through the sheath of the second leg of the tweezers towards the inside of the first leg of the tweezers, as known from DE 3 110 666 C2.

Here, the insulation can be improved such that the fastening element for the pin of the stop element comprises an insulating material and the pin comprises metal. The protrusion or head provided at the pin can be connected to the pin in one piece. The pin can therefore be screw or nail shaped and be produced in an accordingly simple fashion.

For the assembly of the stop element and the counter stop element it is particularly beneficial when the opening in at least one of the legs of the tweezers or the openings in both legs of the tweezers are provided with at least one stop in their axial progression for inserting the counter stop element and/or the fastening element for the pin with an expanded cross-section in the direction of the interior space between the two legs of the tweezers, thus these openings enlarge at least at one stop from the inside towards the outside, and when the parts that can be inserted from the outsides of the legs of the tweezers into these openings, thus the counter stop element and/or the fastening element for the pin with the protrusion or head have at least one radial projection or protrusion for engaging behind the stop, which protrusion may particularly be formed from several individual protrusions and/or one protrusion encircling a portion or the entire perimeter, in particular with a serrated cross-section. This results in a simple snap connection for the respective part at the corresponding leg of the tweezers. The counter stop element and/or the fastening element for the pin therefore only needs to be pressed from the outside into the respective opening, with the radial protrusion or protrusions first being compressed slightly until they open at the stop and thus snap due to the elastic force of the material of the counter stop element and/or the fastening element at the expansion of the cross-section.

It is useful when the faces of the fastening element for the pin, on the one hand, and the counter stop element, on the other side, facing each other are embodied as centering elements. In this manner, when closing the legs of the tweezers, similar to the arrangement according to DE 3 110 666 C2, a precise mutual position of the operational tips or the operational ends of the tweezers can be ensured in the closed position.

Here, the fastening element may have at its face at least one recess, into which the face of the counter stop element or any elevation provided there fits in a centering manner or that the counter stop element can be provided at its face with at least one recess to center an elevation matching thereto at the fastening element in a form-fitting manner. It is particularly beneficial for a simple production and assembly when the recess serving for centering is arranged concentrically in reference to the pin, in particular at its fastening element. This way, the pin ensures at least in case of larger lateral deviations of the tweezers movement a secure guidance of the counter stop element in the centering opening which may be embodied as a concave rounding similar to the face of the counter stop element.

Primarily in combinations of individual or several of the above-mentioned features and measures coagulation tweezers are provided, in which the opening path of the legs of the tweezers remains limited and a good centering is possible; however, the movement of the legs of the tweezers in reference to each other occurs practically without any friction and the production and assembly is facilitated.

BRIEF DESCRIPTION OF THE DRAWINGS

In the following, an exemplary embodiment of the invention is described in greater detail using the drawing. It shows in a partially schematic representation:

FIG. 1 a perspective view and

FIG. 2 a side view of coagulation tweezers according to the invention having two legs of the tweezers mobile in reference to each other, in which the opening path is limited, FIG. 3 a cross-section of the legs of the tweezers taken along the cross-section line A-A in FIG. 2 in the limited open position, FIG. 4 a view according to FIG. 3 during the compression of the two legs of the tweezers, and FIG. 5 a view showing the closed position of the two legs of the tweezers after the compression in the area of the parts provided to limit the opening path.

DETAILED DESCRIPTION OF THE PREFERRED EMBODIMENTS

Coagulation tweezers, in their entirety marked 1, having legs 2 and 3 which merge at a common connection end 5 are provided, with the operational tips 4 and the connection end 5 even in the closed position of the operational tips 4, i.e. at their mutual contact, being spaced apart at a distance from each other (cf. FIG. 5), which have a limited opening of the legs of the tweezers 2 and 3, i.e. the legs of the tweezers 2 and 3 can only be moved apart or pivoted from each other to a limited extent. This way, the operational tips 4 of the tweezers 1 can be held, even in the open position, comparatively close to each other, so that the tweezers can be inserted into a respective bodily orifice at a constant distant without requiring any manual compression.

For limiting the opening, inside the perimeter of the coagulation tweezers 1, a stop element, in its entirety marked 6, and a counter stop element 7 are provided on the legs 2 and 3 of the tweezers. In FIGS. 1 and 2, the electric connectors 8 of the coagulation tweezers 1 are discernible at the connection end 5.

The stop element 6 is provided in the exemplary embodiment as a pin or shaft 9, in the following called "pin 9", having at its free end a lateral or radial protrusion or a head 10, in the following called "head 10", and mounted with the end facing away from this protrusion or head 10 at or in the first leg 2 of the tweezers in a manner remaining to be described.

The counter stop element 7 is provided as a part mounted to the second leg 3 of the tweezers, penetrated by the stop element 6, with its penetration opening 11 having a smaller cross-section than the protrusion or head 10 of the stop element 6. In FIG. 3, it is clearly discernible that the head 10, contrary to the pin 9, can not penetrate this opening 11, but contacts its brim in the open position of the legs of the tweezers and stops, and thus prevents any further movement apart of the legs 2 and 3 of the tweezers. Here, it can be brought into this operational position such that it is pushed with its pin 9 from the outside through the counter stop element, open in the axial direction, through the opening 11 and that it can be fixed at the first leg 2 of the tweezers in a manner remaining to be described.

In FIGS. 3 through 5 it is clearly discernible that the protrusion or head 10, which is movable in reference to the inside of the counter stop element 7 during opening or closing of the legs 2 and 3 of the tweezers, is spaced apart by a distance in the radial direction from the counter stop element 7 and its internal longitudinal cavity 12, so that the closing movement, discernible subsequently in FIGS. 3 through 5, and vice versa the respective opening motion can occur without the head 10 and the counter stop element 7 contacting.

Here, it is discernible from FIGS. 3 and 5 that the head 10 is spaced apart by a radial distance in reference to the interior or the interior cavity 12 of the counter stop element 7 over the entire pivotal path, and thus can remain without contact, when the legs of the tweezers are not also moved unintentionally in a direction perpendicular to their opening or closing movement, which is then restricted by the cooperation of the stop element 6 and the counter stop element 7.

In the exemplary embodiment, the head 10 of the stop element 6 is located at a distance in the radial direction from the inside of the interior longitudinal cavity of the counter stop element at the position equivalent to the opening of the tweezers 1 and also in the closed position. The first phase of the closing motion also remains free and undisturbed from any friction between the head 10 and the counter stop element 7.

In the exemplary embodiment, the counter stop element 7 is a sheath-shaped hollow body or a part of a sheath, which at its intermediate space between the legs 2 and 3 of the tweezers has a base or floor 14 with a penetrating opening 11 for the pin 9 of the stop element 6. This provides inside the interior longitudinal cavity 12 in the stop element 7, on the one hand, sufficient space for a friction-free movement of the head 10 and, on the other hand, a stop for this head 10 at the limited, largest possible opening or distance of the two legs 2 and 3 of the tweezers.

In FIGS. 3 to 5 it is further discernible that the cross-section of the penetrating opening 11 of the hollow body or the sheath part is larger than the cross-section of the pin 9 and that the edge of the penetrating opening 11 is provided with and maintains such a radial distance from the pin 9, that the pin 9 during the pivoting of the legs of the tweezers can be moved over the entire or at least a part of the pivotal path with play or without any contact through the penetrating opening 11, as long as the legs 2 and 3 of the tweezers are not accidentally displaced perpendicularly in reference to this opening and closing motion. Due to the fact that this distance and/or this play is relatively small, such a lateral displacement motion is also very small so that the legs 2 and 3 of the tweezers, at least in the closing position according to FIG. 5, fit well into a mutual centering still to be described.

The hollow body or sheath part of the counter stop element 7 here comprises electrically insulating material in order to maintain or provide the insulation of the legs 2 and 3 of the tweezers from each other as good as possible.

In FIGS. 3 to 5 it is discernible that the counter stop element 7, i.e. the sheath part, is provided such that it can be inserted and impressed and/or mounted to the exterior in a form-fitting manner, in the exemplary embodiment in a snapping form, facing away from the first leg 2 of the tweezers into the second leg 3 of the tweezers in an opening 15 arranged there. Here, the counter stop element 7 embodied as a sheath or sheath part has a brim or protrusion 17 contacting the outside of the second leg 3 of the tweezers (in which it is supported) or an insulating coating 16 provided thereat, which approximately encircles it flange-like and further improves the insulation. Here, this flange-like encircling edge 17 allows an additional fastening with adhesives or sealants at the transfer of the insulating coating 16 to the opening 15 in order to improve the insulation and also the fastening.

In order to anchor the pin 9 of the stop element 6 to the first leg 2 of the tweezers, in the exemplary embodiment, a fastening element 18, which can be inserted into the outside of the leg 2 which is provided with an insulating coating 16, includes a flange or edge 19, which is approximately equivalent to the edge 17 of the counter stop element 7 with regard to function and form. In this fastening element 18, the pin 9 which protrudes towards the intermediate space of the legs 2 and 3 of the tweezers, is fastened, perhaps connected in one piece, when its head 10 could subsequently be mounted to the pin 9 from the opening and the interior longitudinal cavity 12, in the exemplary embodiment, however, for example screwed or non-detachably inserted into the fastening element 18. Here, in the interest of a best possible insulation, the fastening element 18 comprises an insulating material, while the pin 9 may be made from metal in order to have a good strength in spite of its very small dimension. Here, in this exemplary embodiment, the head 10 provided at the pin 9 is connected in one piece to the pin 9. For the assembly, the pin 9 can be pushed, for example through an interior of the longitudinal cavity 12 of the stop element 7, after its mounting to the second leg 3 of the tweezers, and screwed or impressed or glued into the fastening element 18 previously inserted into the first leg 2 of the tweezers.

In FIGS. 3 through 5, it is discernible that the openings 15 in the two legs 2 and 3 of the tweezers for inserting the fastening element 18 for the pin 9 and for inserting the counter stop element 7 in the axial progression are provided with a stop 20 having a widened cross-section in a direction towards the interior space between the two legs 2 and 3 of the tweezers. At the sides of the legs 2 and 3 of the tweezers facing each other, the openings 15 have therefore a larger cross-section than at the exterior sides, because the respective stop 20 encircles the entire perimeter.

The parts that can be inserted from the exterior of the legs 2 and 3 of the tweezers into these openings 15, i.e. the fastening element 18 for the stop element 6, on the one hand, and the counter stop element 7, on the other hand, have a radial protrusion 21 for engaging the respective stop 20, protruding in reference to the exterior perimeter, as shown in FIGS. 3 through 5. This protrusion 21 is here beneficially a protrusion encircling the entire perimeter, in particular, with a serrated cross-section. This results in a snap connection of the fastening element 18 in the leg 2 of the tweezers and the counter stop element 7 in the leg 3 of the tweezers, which may be supported by a pressure seat or perhaps adhesion. In this way, it is possible to prevent the fastening element 18 and/or the counter stop element 7, which are in the mutual contact when the two tweezers legs 2 and 3 are pressed together, (compare FIG. 5) from being compressed and pressed out of the legs of the tweezers.

For a mutual precise approach of the operational tips 4, a centering in the closing position of the legs 2 and 3 of the tweezers according to FIG. 5 is provided such that the faces of the fastening element 18 and the counter stop element 7 facing each other are embodied as mutual centering means. Here, it is discernible that the fastening element 18 at its face has a concavely rounded recess 22, into which the face 13 of the counter stop element 7 fits in a form-fitting manner, as clearly discernible primarily from FIG. 5. It is also possible that the counter stop element 7 at the face is at least provided with a recess for a form-fitting match of a centering elevation at the fastening element 18.

The recess 22 serving for centering is here arranged concentrically at the pin 9 protruding at the face of the fastening element 18 so that in case of an undesired lateral movement of the legs 2 and 3 of the tweezers in reference to each other, both the pin 9 with the penetrating opening 11 as well as the recess 22 with the face 13 ensure a precise approach of the operational tips 4.

The coagulation tweezers 1 are provided with two legs 2 and 3, with their mutual pivoting apart being limited by a stop element 6 and a counter stop element 7. Here, the protrusion or head 10 of the stop element 6, when opening or closing the legs 2 and 3 of the tweezers is spaced at a distance in the radial direction during relative displacement or movement along its pivotal path in reference to the interior longitudinal cavity 12 of the counter top element 7 so that during normal leg movements of the tweezers no friction develops by these stop elements.

The invention claimed is:

1. Coagulation tweezers (1), comprising first and second legs (2, 3) that merge from operational tips (4) thereof towards a common connection end (5), and which are spaced apart from one another between the operational tips (4) and the connecting end (5) even in a closing position of the operational tips (4), a stop element (6) and a counter stop element (7) located inside a perimeter of the coagulation tweezers (1) for limiting an opening of the legs of the tweezers, the stop element (6) comprising a pin or a shaft (9) with a lateral or radial protrusion or head (10) arranged at a free end thereof and with an end facing away from the protrusion or head (10) fastened in the first leg (2) of the tweezers, and the counter stop element (7) comprising a part mounted in the second leg (3) that is penetrated by the stop element (6) and having a penetrating opening (11) with a smaller cross-section than the protrusion or head (10) of the stop element (6), and during opening or closing of the legs (2, 3) of the tweezers, the protrusion or head (10) is movable inside the counter stop element (7), which is spaced apart at a distance in the radial direction from the protrusion or head (10) during relative displacement between the head and the counter stop element (7).

2. Coagulation tweezers according to claim 1, wherein the protrusion or head (10) is spaced apart by a radial distance over an entire pivotal path in reference to an interior of the counter stop element (7).

3. Coagulation tweezers according to claim 1, wherein the protrusion or head (10) of the stop element (6) is at least spaced apart by a distance in the radial direction from the inside of the counter stop element (7) at least in the opening position of the legs (2, 3) of the tweezers or in both end positions.

4. Coagulation tweezers according to claim 1, wherein the counter stop element (7) is a hollow body or cage or sheath part extending axially approximately in a direction of a pivotal motion of the legs, which has at a face (13) thereof, located in an intermediate space between the legs (2, 3) of the tweezers, a connection or base (14) with the penetrating opening (11) for the pin (9) or the shaft of the stop element (6).

5. Coagulation tweezers according to claim 4, wherein a cross-section of the penetrating opening (11) of the hollow body or cage or sheath part of the counter stop element (7) is larger than a cross-section of the pin (9) or the shaft of the stop element and an edge of the penetrating opening (11) has a sufficient radial distance from the pin (9) or the shaft of the stop element so that the pin (9) or the shaft of the stop element can be moved with play or without any contact through the penetrating opening (11) during the pivoting motion of the legs (2, 3) of the tweezers over an entire or at least part of the pivotal path.

6. Coagulation tweezers according to claim 4, wherein the hollow body or cage or sheath part comprises electrically insulating materials.

7. Coagulation tweezers according to claim 1, wherein the counter stop element (7) is inserted or mounted in a form-fitting manner at an outside, facing away from the first leg (2) of the tweezers, into the second leg (3) of the tweezers in an opening (15) provided there.

8. Coagulation tweezers according to claim 1, wherein the counter stop element (7) embodied as the hollow body or cage or sheath part has a contacting edge (17) or protrusion that extends in a flange-like manner located at an outside of the second leg (2) of the tweezers or an insulating coating (16) provided thereat which support the contacting edge or protrusion.

9. Coagulation tweezers according to claim 1, wherein for anchoring the pin (9) or the shaft of the stop element (6) to the first leg (2) of the tweezers, a fastening element (18) is inserted from outside and is provided with a brim, flange, or protrusion, in which the pin (9) or the shaft of the stop element is mounted protruding towards an intermediate space between the legs (2, 3) of the tweezers.

10. Coagulation tweezers according to claim 9, wherein the fastening element (18) for the pin or the shaft of the stop element is made from isolating material and the pin (9) is made from metal.

11. Coagulation tweezers according to claim 1, wherein the protrusion or head (9) provided for the pin (9) is connected to the pin (9) in one piece.

12. Coagulation tweezers according to claim 1, further comprising an opening (15) in at least one of the legs of the tweezers or openings (15) in both of the two legs of the tweezers, at least one of the counter stop element (7) or a fastening element (18) for the pin (9) or the shaft of the stop element in an axial progression of the opening has at least one stop (20) with a cross-sectional widening in a direction towards the interior distance of the two legs (2, 3) of the tweezers, and at least one of the counter stop element (7) or the fastening element (18) for the stop element (6) is inserted from outside into the openings and have at least one radial projection or protrusion (21) to engage the stop (20) which is formed by several individual protrusions or a protrusion extending from an entire perimeter.

13. Coagulation tweezers according to claim 12, wherein the fastening element (18) and the counter stop (7) include faces that face one another and are formed as a mutual centering arrangement for the pin (9) or the shaft of the stop element and the counter stop element (7).

14. Coagulation tweezers according to claim 13, wherein the face of the fastening element (18) has at least one recess (22) in which the face (13) of the counter stop element (7) is received or an elevation provided at the face (13) of the counter stop element fits in a centering manner, or the face of the counter stop element (7) has at least one recess matching a centering elevation at the fastening element (18) in a form-fitting manner.

15. Coagulation tweezers according to claim 14, wherein the pin (9) or the shaft of the stop element is arranged for centering in the recess (22), and the recess is concave.

* * * * *